(12) United States Patent
Chisolm et al.

(10) Patent No.: US 7,731,136 B1
(45) Date of Patent: Jun. 8, 2010

(54) COMBINED IV BAG AND OXYGEN SUPPORTING POLE AND ASSOCIATED METHOD

(76) Inventors: Cory Chisolm, 54 Richard Lee La., Phoenixville, PA (US) 19460-1914; Gary Chisolm, 54 Richard Lee La., Phoenixville, PA (US) 19460-1914

( * ) Notice: Subject to any disclaimer, the term of this patent is extended or adjusted under 35 U.S.C. 154(b) by 233 days.

(21) Appl. No.: 12/077,472

(22) Filed: Mar. 19, 2008

Related U.S. Application Data

(60) Provisional application No. 60/918,574, filed on Mar. 19, 2007.

(51) Int. Cl.
*A47K 1/04* (2006.01)
(52) U.S. Cl. ...................... 248/129; 248/125.1; 211/204
(58) Field of Classification Search .............. 248/122.1, 248/129, 125.1
See application file for complete search history.

(56) References Cited

U.S. PATENT DOCUMENTS

| | | | | |
|---|---|---|---|---|
| 3,960,398 A * | 6/1976 | Johnson ........................ 294/16 |
| 3,970,344 A * | 7/1976 | Baumann ................ 297/188.02 |
| 4,213,648 A * | 7/1980 | Steichen ................... 297/188.2 |
| 4,506,903 A * | 3/1985 | Bowermaster ........... 280/304.1 |
| 4,696,420 A * | 9/1987 | Kulik .......................... 224/275 |
| 4,832,294 A | 5/1989 | Eidem |
| 5,123,409 A * | 6/1992 | Sheffield et al. ........ 128/204.18 |
| 5,340,140 A * | 8/1994 | Bynum ..................... 280/304.1 |
| 5,632,268 A * | 5/1997 | Ellis et al. .............. 128/204.18 |
| 6,182,662 B1 * | 2/2001 | McGhee ..................... 128/845 |
| 6,375,133 B1 | 4/2002 | Morrow |
| 6,405,882 B1 * | 6/2002 | Baxter ...................... 211/85.18 |
| 6,431,505 B2 | 8/2002 | Chinn |
| 7,188,855 B1 * | 3/2007 | Thomas ................... 280/304.1 |
| 7,243,666 B2 * | 7/2007 | Carroll ......................... 135/67 |
| 7,494,139 B2 * | 2/2009 | Turner et al. ........... 280/87.021 |
| 2005/0113668 A1 * | 5/2005 | Srinivasan .................. 600/411 |
| 2007/0267453 A1 * | 11/2007 | Carroll ........................ 224/407 |
| 2008/0272571 A1 * | 11/2008 | Turner et al. ................ 280/202 |

* cited by examiner

*Primary Examiner*—J. Allen Shriver, II
*Assistant Examiner*—Alaeddin Mohseni

(57) ABSTRACT

A multifunctional medical equipment supporting apparatus effectively includes a mobile frame, a telescopically adjustable shaft, and a concave base member with an annular outer circumference raised above a ground surface. Such a base member is statically affixed to the female member and spaced from the male member, and a plurality of casters are pivotally coupled to an underside of the base member and equidistantly juxtaposed along the outer circumference. The apparatus further includes a mechanism for receiving and maintaining an existing oxygen tank adjacently positioned to the frame such that the existing oxygen tank is automatically raised from an initial lowered position to an elevated position as an oxygen volume is depleted from the existing oxygen tank. A mechanism for conveniently receiving and suspending a plurality of existing intra-venous fluid-dispensing bags is located adjacent to a top portion of the frame.

14 Claims, 3 Drawing Sheets

COMBINED IV BAG AND OXYGEN SUPPORTING POLE AND ASSOCIATED METHOD

CROSS REFERENCE TO RELATED APPLICATIONS

This application claims the benefit of U.S. Provisional Application No. 60/918,574, filed Mar. 19, 2007, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to medical equipment and, more particularly, to a combined IV bag and oxygen supporting pole for supporting medical equipment.

2. Prior Art

For many years, intravenous (I.V.) solutions have been administered in a fairly simple fashion with a bottle or bag of solution hanging from a pole on a simple tripod base stand. Many varieties of IV poles exist in the field for supporting intravenous fluid containers to facilitate the gravity feed of fluids contained therein to patients oriented in an adjacent support structure, such as an emergency cot or bed. Such fluids are traditionally administered in hospitals and there is little, if any need for transport of such stands and other associated equipment. Recently, several advances in medicine have rendered such equipment obsolete. While conventional I.V. stands are portable in the broadest sense, they remain heavy and cumbersome to transport.

The spread of the use of I.V. equipment to the home has rendered existing I.V. stands inadequate for several reasons. In the home, the patient is often reasonably ambulatory and thus, it is highly desirable to transport the I.V. stand and associated equipment with the patient about the house. Homes typically have various irregular surfaces which are not easily accommodated by conventional I.V. stands. In particular, such surfaces are stairs, carpets and any other surfaces which are not typical in an institutional setting. Furthermore, many patients require the administration of multiple I.V. fluids. Unfortunately, most I.V. stands only provide suspension means for one I.V. bag, thus requiring the user to have multiple I.V. stands that effectively prevent them from moving about independently. Some patients also receive supplemental oxygen as part of their treatment. Such oxygen is administered to the patient from an oxygen tank that is rather heavy and is thus placed on a portable cart or similar assembly. Again, having both an I.V. stand and an oxygen tank cart can prevent a patient from moving about their home or hospital room independently.

U.S. Pat. No. 4,832,294 to Eidem discloses a portable stand which is provided for the transport of infusion pumps, intravenous solutions and other associated equipment. The stand consists of a T-shaped base having a base member with a base leg extending perpendicularly therefrom. Large, diameter non-swiveling wheels are located at either end of the base member and the caster wheel is located at the end of the base leg. A skid member is provided to assist in the transport of the stand on stairs. A cylinder support platform may be affixed to the T-shaped base. Unfortunately, this prior art example does not combine an I.V. pole and an oxygen tank, thereby keeping the necessities together and reducing cluttered space.

U.S. Pat. No. 6,375,133 to Morrow discloses an intravenous (IV) support assembly including a mounting adapter and an upright IV pole. The mounting adapter is mountable to a single rail of a patient support frame, and includes an insertion member and a locking mechanism. The IV pole is supported by the mounting adapter, and includes a hollow lower end for receiving the insertion member of the mounting adapter. The IV pole is secured to the insertion member by the locking mechanism of the insertion member. A variety of different mounting adapters each configured for a different rail configuration are available for supporting a common IV pole, so the IV pole is transferable between mounting adapters mounted to different rails. Unfortunately, this prior art example is not designed to reduce tripping hazards and thereby provide a safer environment for staff and patients alike.

U.S. Pat. No. 6,431,505 to Chinn discloses a an IV pole having mounted at an upper end a holding assembly comprising a head and a plunger, and at a lower end a docking assembly. The head on an upper portion includes at least two opposed upwardly extending projections suitably for hanging IV fluid containers. The plunger is movable between an extended position in which the plunger is held a distance above the height of the projections, and a retracted position in which the plunger is proximate to the projections such that removal of IV fluid containers hung on the projections is prevented. The smooth profile of the head and plunger greatly reduces the risk of the IV pole getting snagged on an obstruction or causing injury to rescue personnel. The docking assembly permits the IV pole to be removably secured to a docking port provided to a structural member and to be lowered to a stowed position. Unfortunately, this prior art example is not designed to make the hassle of juggling patients and vital life support equipment much more efficient and easier.

Accordingly, the present invention is disclosed in order to overcome the above noted shortcomings. The IV bag and oxygen supporting pole is convenient and easy to use, lightweight yet durable in design, and designed for supporting medical equipment. The apparatus is simple to use, inexpensive, and designed for many years of repeated use.

BRIEF SUMMARY OF THE INVENTION

In view of the foregoing background, it is therefore an object of the present invention to provide an apparatus for supporting medical equipment. These and other objects, features, and advantages of the invention are provided by a multifunctional medical equipment supporting apparatus.

A multifunctional medical equipment supporting apparatus effectively includes a mobile frame. Such a mobile frame includes a telescopically adjustable shaft including selectively interlocked rectilinear male and female members and a concave base member with an annular outer circumference raised above a ground surface. Such a base member is statically affixed to the female member and spaced from the male member, and a plurality of casters are pivotally coupled to an underside of the base member and equidistantly juxtaposed along the outer circumference.

The apparatus further includes a mechanism for receiving and maintaining an existing oxygen tank adjacently positioned to the frame such that the existing oxygen tank is automatically raised from an initial lowered position to an elevated position as an oxygen volume is depleted from the existing oxygen tank. Such lowered and elevated positions are conveniently defined at opposed ends of a linear path registered parallel to a central portion of the frame. The receiving and maintaining mechanism includes a weight member provided with a longitudinal length registered parallel to a longitudinal length of the female member and is spaced therefrom.

A plurality of rectilinear support arms is pivotally coupled directly to the female member, and such support arms are further pivotally coupled directly to the weight member. A plurality of anchor brackets is pivotally coupled to the supports arms and diametrically offset from the weight member such that the anchor brackets maintain a fixed linear spatial distance from the weight member while traveling along the linear path. The existing oxygen tank is removably positioned within the anchor brackets and interfitted therebetween, and the weight member has a center of mass selectively offset from a center of mass of the existing oxygen tank as the oxygen level is depleted therefrom.

Each of the support arms has axially opposed first and second ends advantageously terminating laterally away from the female member respectively, and the weight member is pivotally coupled directly to each of the first ends of the support arms such that each of the support arms are synchronously pivoted from a horizontal position to an angularly offset position as the weight member downwardly travels along the linear path. The weight member is vertically oriented and juxtaposed parallel to the female member while the support arms are synchronously pivoted to the angularly offset position.

The anchor brackets are pivotally coupled to each of the second ends of the support arms respectively and are effectively maintained at a horizontal position and further are vertically aligned when the support arms are biased to the angularly offset position and further while the weight member downwardly travels along the linear path. The existing oxygen tank has a center of mass disposed above a center of mass of the weight member after the support arms are pivoted to the angularly offset position.

The apparatus further includes a mechanism for conveniently receiving and suspending a plurality of existing intra-venous fluid-dispensing bags adjacent to a top portion of the frame. Such a receiving and suspending mechanism includes a ring and a plurality of coplanar shafts directly coupled thereto. Such a ring is concentrically attached to the male member, and each of the shafts radially extends out from the ring and is equidistantly spaced thereabout. Each of the shafts further has a curvilinear loop formed at a distal end thereof for receiving one of the pluralities of existing intra-venous fluid-dispensing bags respectively. The receiving and maintaining mechanism cooperates with the receiving and suspending mechanism so that the frame is balanced at an upright and vertical orientation during transportation between remote locations.

A method for simultaneously supporting and transporting an existing oxygen tank and a plurality of existing intra-venous fluid-dispensing bag includes the steps of: providing a mobile frame; receiving and maintaining the existing oxygen tank adjacently positioned to the frame; automatically raising the existing oxygen tank from an initial lowered position to an elevated position as an oxygen volume is depleted from the existing oxygen tank, the lowered and elevated positions being defined at opposed ends of a linear path registered parallel to a central portion of the frame; receiving and suspending the plurality of existing intra-venous fluid-dispensing bags adjacent to a top portion of the frame; and maintaining the frame balanced at an upright and vertical orientation during transportation between remote locations.

The method further includes the steps of: providing a telescopically adjustable shaft including selectively interlocked rectilinear male and female members; providing a concave base member with an annular outer circumference raised above a ground surface; statically affixing the base member to the female member by spacing the base member from the male member; and providing and pivotally coupling a plurality of casters to an underside of the base member by equidistantly juxtaposing the casters along the outer circumference.

The method further includes the steps: providing and registering a longitudinal length of a weight member parallel to a longitudinal length of the female member by spacing the weight member from the female member; providing and pivotally coupling a plurality of rectilinear support arms directly to the female member; pivotally coupling the support arms directly to the weight member; providing and pivotally coupling a plurality of anchor brackets to the supports arms by diametrically offsetting the anchor brackets from the weight member; removably positioning and interfitting the existing oxygen tank within the anchor brackets; maintaining a fixed linear spatial distance between the anchor brackets and the weight member while the anchor brackets travel along the linear path; and selectively offsetting a center of mass of the weight member from a center of mass of the existing oxygen tank as the oxygen level is depleted therefrom.

The method further includes the steps of: synchronously pivoting the support arms from a horizontal position to an angularly offset position as the weight member downwardly travels along the linear path; and maintaining the weight member at a vertically oriented position such that the weight member is juxtaposed parallel to the female member while the support arms are synchronously pivoted to the angularly offset position.

The method further includes the steps of: maintaining the anchor brackets at a horizontal position; and vertically aligning the anchor brackets when the support arms are biased to the angularly offset position and further while the weight member downwardly travels along the linear path.

The method further includes the steps of: providing a ring and a plurality of coplanar shafts directly coupled thereto; and respectively positioning the plurality of existing intra-venous fluid-dispensing bags on a plurality of curvilinear loops formed at a distal end of each of the shafts.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

Figure 1:
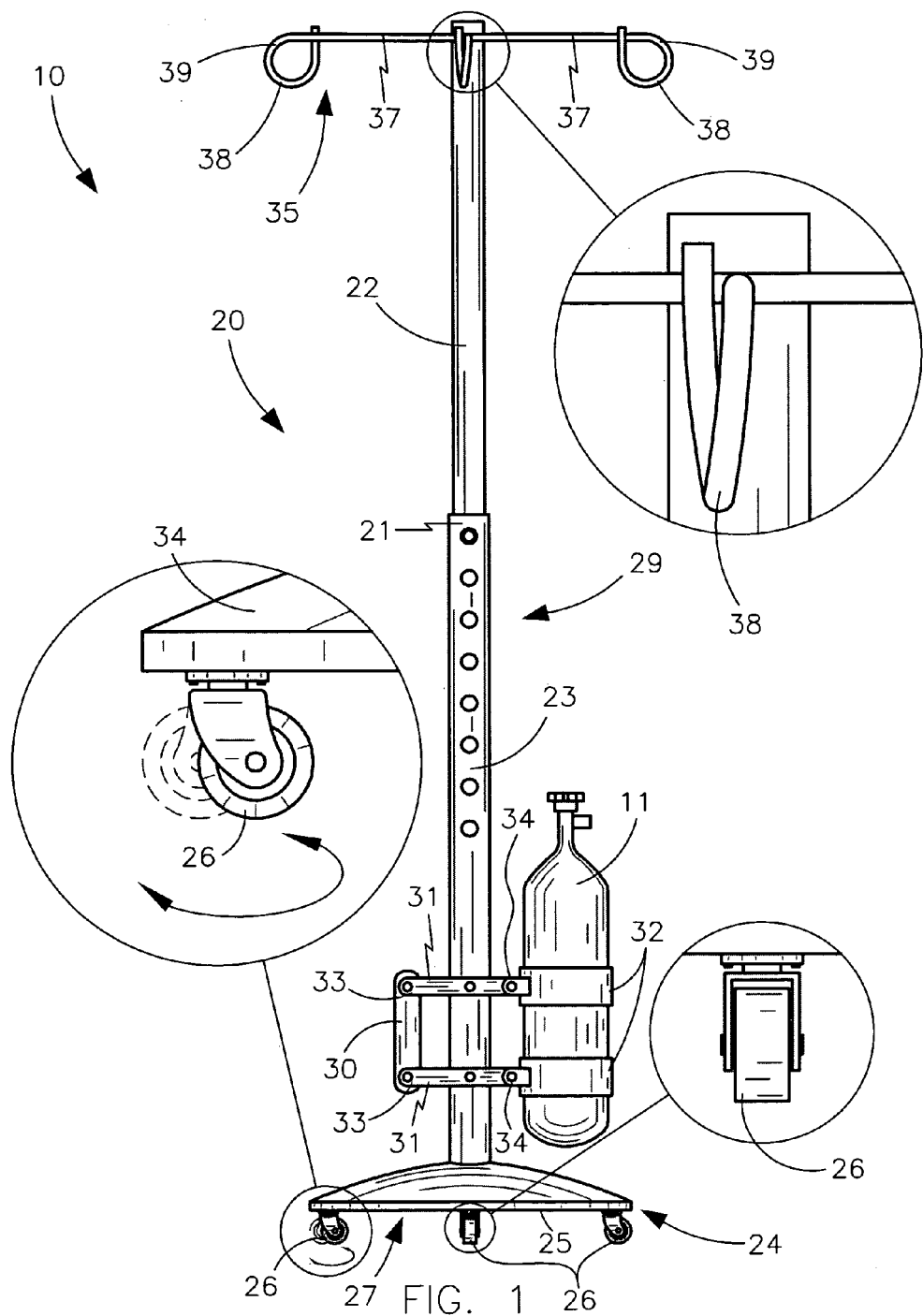
FIG. 1 is a front elevational view showing a multifunctional medical equipment supporting apparatus, with enlarged views of the casters and a curvilinear loop respectively; in accordance with the present invention.
Figure 2:
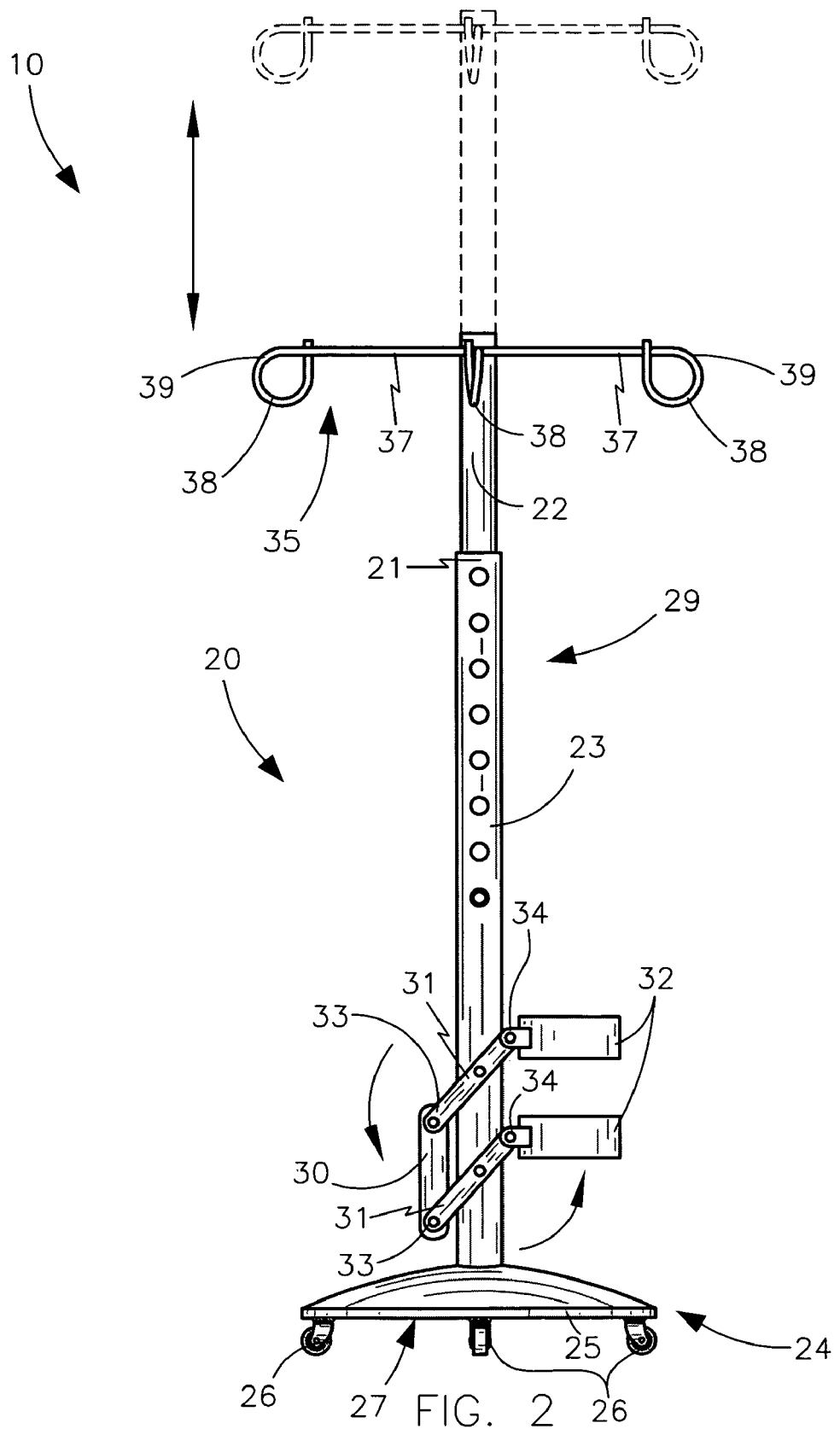
FIG. 2 is a front elevational view showing the pivoting movement of the weight member and brackets, in accordance with the present invention.
Figure 3:
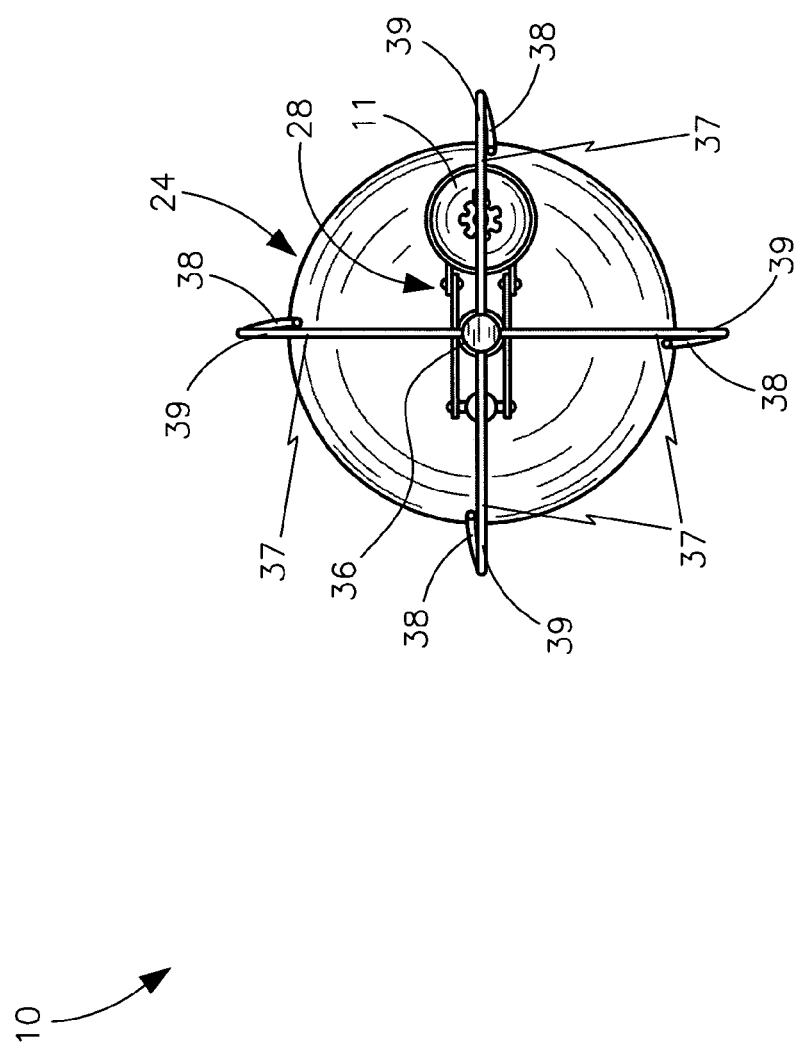
FIG. 3 is a top planar view of the multifunctional medical equipment supporting apparatus, in accordance with the present invention.

The apparatus of this invention is referred to generally in FIGS. 1-3 by the reference numeral 10 and is intended to protect a multifunctional medical equipment supporting apparatus. It should be understood that the apparatus 10 may be used to support many different types of medical equipment and should not be limited to supporting only those types of medical equipments mentioned herein.

Referring initially to FIGS. 1, 2 and 3, a multifunctional medical equipment supporting apparatus 10 includes a mobile frame 20. Such a mobile frame 20 includes a telescopically adjustable shaft 21 including selectively interlocked rectilinear male and female members 22, 23 and a concave base member 24 with an annular outer circumference 25 raised above a ground surface. Such a base member 24 is statically affixed to the female member 23 and spaced from the male member 22, and a plurality of casters 26 are pivotally coupled to an underside 27 of the base member 24 and equidistantly juxtaposed along the outer circumference 25. The casters 26 enable a user to easily move the apparatus as the user walks around the house.

Referring again to FIGS. 1, 2 and 3, the apparatus 10 further includes a mechanism 28 for receiving and maintaining an existing oxygen tank 11 adjacently positioned to the frame 20 which is important such that the existing oxygen tank 11 is automatically raised from an initial lowered position to an elevated position as an oxygen volume is depleted from the existing oxygen tank 11. Such lowered and elevated positions are defined at opposed ends of a linear path registered parallel to a central portion 29 of the frame 20.

The receiving and maintaining mechanism 28 includes a weight member 30 provided with a longitudinal length registered parallel to a longitudinal length of the female member 23 and is spaced therefrom. A plurality of rectilinear support arms 31 is pivotally coupled directly, without the use of intervening elements, to the female member 23, and such support arms 31 are further pivotally coupled directly, without the use of intervening elements, to the weight member 30. A plurality of anchor brackets 32 is pivotally coupled to the supports arms 31 and diametrically offset from the weight member 30 which is crucial such that the anchor brackets 32 maintain a fixed linear spatial distance from the weight member 30 while traveling along the linear path. The existing oxygen tank 11 is removably positioned within the anchor brackets 32 and interfitted therebetween, and the weight member 30 has a center of mass selectively offset from a center of mass of the existing oxygen tank 11 as the oxygen level is depleted therefrom. The receiving and maintaining mechanism 28 automatically articulates upwardly when not in use, thereby consuming less space.

Each of the support arms 31 has axially opposed first and second ends 33, 34 terminating laterally away from the female member 23 respectively, and the weight member 30 is pivotally coupled directly, without the use of intervening elements, to each of the first ends 33 of the support arms 31 which is vital such that each of the support arms 31 are synchronously pivoted from a horizontal position to an angularly offset position as the weight member 30 downwardly travels along the linear path. The weight member 30 is vertically oriented and juxtaposed parallel to the female member 23 while the support arms 31 are synchronously pivoted to the angularly offset position.

The anchor brackets 32 are pivotally coupled to each of the second ends 34 of the support arms 31 respectively and are maintained at a horizontal position and further are vertically aligned when the support arms 31 are biased to the angularly offset position and further while the weight member 30 downwardly travels along the linear path. The existing oxygen tank 11 has a center of mass disposed above a center of mass of the weight member 30 after the support arms 31 are pivoted to the angularly offset position.

Referring again to FIGS. 1, 2 and 3, the apparatus 10 further includes a mechanism 35 for receiving and suspending a plurality of existing intra-venous fluid-dispensing bags adjacent to a top portion of the frame 20. Such a receiving and suspending mechanism 35 includes a ring 36 and a plurality of coplanar shafts 37 directly coupled thereto, without the use of intervening elements. Such a ring 36 is concentrically attached to the male member 22, and each of the shafts 37 radially extends out from the ring 36 and is equidistantly spaced thereabout. Each of the shafts 37 further has a curvilinear loop 38 formed at a distal end 39 thereof for receiving one of the pluralities of existing intra-venous fluid-dispensing bags respectively. The receiving and maintaining mechanism 35 cooperates with the receiving and suspending mechanism 28 so that the frame 20 is balanced at an upright and vertical orientation during transportation between remote locations.

The apparatus includes the elongated and vertical telescopically adjustable shaft that has a plurality of shafts and loops monolithically formed at the top end thereof. A base member is directly attached, without the use of intervening elements, to the bottom end of the shaft. Such a shaft, loops and base member may be produced from chrome, which is crucial for providing many years of reliable use. The assembly may include a plurality of loops for the placement of IV bags. Of course, the apparatus may be produced with a lesser or greater amount of loops depending on the intended use thereof, as is obvious to a person of ordinary skill in the art. A first and second group of four loops may be positioned on each side of the receiving and suspending mechanism, at equally spaced intervals.

A plurality of casters is directly attached, without the use of intervening elements, to the bottom surface of the base member. Such caster wheels may be spaced apart at 90° intervals, which is essential and advantageous for equal weight distribution. Each caster may further have a two-wheel locking design that is important and advantageous for easy mobility and safety. The shaft is telescopically adjustable in height and may be easily adjusted by depressing a push-button that protrudes through one of a plurality of annular apertures. The base member also has brackets monolithically formed therewith, in which an oxygen tank can conveniently be placed. A weight member may be positioned on the opposite side of the base that is crucial for compensating for the weight of the oxygen tank.

The present invention, as claimed, provides the unexpected and unpredictable benefit of an apparatus that is convenient and easy to use, is durable yet lightweight in design, is versatile in its applications, and provides a practical enhancement to standard IV poles that is most beneficial to medical staff and patients. By combining the IV pole with an oxygen tank, the present invention keeps these necessities together, thus reducing cluttered space. Doing so also helps to reduce tripping hazards by providing a safer environment for staff and patients alike. The present invention also makes the hassle of juggling patients and vital life support equipment much more efficient and easier.

In use, a method for simultaneously supporting and transporting an existing oxygen tank 11 and a plurality of existing intra-venous fluid-dispensing bags includes the steps of: providing a mobile frame 20; receiving and maintaining the existing oxygen tank 11 adjacently positioned to the frame 20; automatically raising the existing oxygen tank 11 from an initial lowered position to an elevated position as an oxygen volume is depleted from the existing oxygen tank 11, the lowered and elevated positions being defined at opposed ends of a linear path registered parallel to a central portion 29 of the frame 20; receiving and suspending the plurality of existing intra-venous fluid-dispensing bags adjacent to a top portion of the frame 20; and maintaining the frame 20 balanced at an upright and vertical orientation during transportation between remote locations.

In use, the method further includes the steps of: providing a telescopically adjustable shaft 21 including selectively interlocked rectilinear male and female members 22, 23; providing a concave base member 24 with an annular outer circumference 25 raised above a ground surface; statically affixing the base member 24 to the female member 23 by spacing the base member 24 from the male member 22; and providing and pivotally coupling a plurality of casters 26 to an underside of the base member 24 by equidistantly juxtaposing the casters 26 along the outer circumference 25.

In use, the method further includes the steps: providing and registering a longitudinal length of a weight member 30 parallel to a longitudinal length of the female member 23 by spacing the weight member 30 from the female member 23; providing and pivotally coupling a plurality of rectilinear support arms 31 directly, without the use of intervening elements, to the female member 23; pivotally coupling the support arms 31 directly, without the use of intervening elements, to the weight member 30; providing and pivotally coupling a plurality of anchor brackets 32 to the supports arms 31 by diametrically offsetting the anchor brackets 32 from the weight member 30; removably positioning and interfitting the existing oxygen tank 11 within the anchor brackets 32; maintaining a fixed linear spatial distance between the anchor brackets 32 and the weight member 30 while the anchor brackets 32 travel along the linear path; and selectively offsetting a center of mass of the weight member 30 from a center of mass of the existing oxygen tank 11 as the oxygen level is depleted therefrom.

In use, the method further includes the steps of: synchronously pivoting the support arms 31 from a horizontal position to an angularly offset position as the weight member 30 downwardly travels along the linear path; and maintaining the weight member 30 at a vertically oriented position such that the weight member 30 is juxtaposed parallel to the female member 23 while the support arms 31 are synchronously pivoted to the angularly offset position.

In use, the method further includes the steps of: maintaining the anchor brackets 32 at a horizontal position; and vertically aligning the anchor brackets 32 when the support arms 31 are biased to the angularly offset position and further while the weight member 30 downwardly travels along the linear path.

In use, the method further includes the steps of: providing a ring 36 and a plurality of coplanar shafts 37 directly coupled thereto; and respectively positioning the plurality of existing intra-venous fluid-dispensing bags on a plurality of curvilinear loops 38 formed at a distal end 39 of each of the shafts 37.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A multifunctional medical equipment supporting apparatus comprising:
   a frame;
   means for receiving and maintaining an existing oxygen tank adjacently positioned to said frame such that the existing oxygen tank is automatically raised from an initial lowered position to an elevated position as an oxygen volume is depleted from the existing oxygen tank, said lowered and elevated positions being defined at opposed ends of a linear path registered parallel to a central portion of said frame; and
   means for receiving and suspending a plurality of existing intra-venous fluid-dispensing bags adjacent to a top portion of said frame.

2. The multifunctional medical equipment supporting apparatus of claim 1, wherein said mobile frame comprises:
   a telescopically adjustable shaft including selectively interlocked rectilinear male and female members;
   a concave base member having an annular outer circumference raised above a ground surface, said base member being statically affixed to said female member and spaced from said male member; and
   a plurality of casters pivotally coupled to an underside of said base member and equidistantly juxtaposed along said outer circumference.

3. The multifunctional medical equipment supporting apparatus of claim 2, wherein said receiving and maintaining means comprises:
- a weight member provided with a longitudinal length registered parallel to a longitudinal length of said female member and being spaced therefrom;
- a plurality of rectilinear support arms pivotally coupled directly to said female member, said support arms further being pivotally coupled directly to said weight member; and
- a plurality of anchor brackets pivotally coupled to said supports arms and diametrically offset from said weight member such that said anchor brackets maintain a fixed linear spatial distance from said weight member while traveling along said linear path;
- wherein the existing oxygen tank is removably positioned within said anchor brackets and interfitted therebetween;
- wherein said weight member has a center of mass selectively offset from a center of mass of the existing oxygen tank as the oxygen level is depleted therefrom.

4. The multifunctional medical equipment supporting apparatus of claim 3, wherein each of said support arms has axially opposed first and second ends terminating laterally away from said female member respectively;
- wherein said weight member is pivotally coupled directly to each of said first ends of said support arms such that each of said support arms are synchronously pivoted from a horizontal position to an angularly offset position as said weight member downwardly travels along said linear path, said weight member being vertically oriented and juxtaposed parallel to said female member while said support arms are synchronously pivoted to said angularly offset position.

5. The multifunctional medical equipment supporting apparatus of claim 4, wherein said anchor brackets are pivotally coupled to each of said second ends of said support arms respectively, said anchor brackets being maintained at a horizontal position and further being vertically aligned when said support arms are biased to said angularly offset position and further while said weight member downwardly travels along said linear path.

6. The multifunctional medical equipment supporting apparatus of claim 5, wherein the existing oxygen tank has a center of mass disposed above a center of mass of said weight member after said support arms are pivoted to said angularly offset position.

7. The multifunctional medical equipment supporting apparatus of claim 2, wherein said receiving and suspending means comprises:
- a ring and a plurality of coplanar shafts directly coupled thereto, said ring being concentrically attached to said male member, each of said shafts radially extending out from said ring and being equidistantly spaced thereabout, each of said shafts having a curvilinear loop formed at a distal end thereof for receiving one of the plurality of existing intra-venous fluid-dispensing bags respectively.

8. A multifunctional medical equipment supporting apparatus comprising:
- a mobile frame;
- means for receiving and maintaining an existing oxygen tank adjacently positioned to said frame such that the existing oxygen tank is automatically raised from an initial lowered position to an elevated position as an oxygen volume is depleted from the existing oxygen tank, said lowered and elevated positions being defined at opposed ends of a linear path registered parallel to a central portion of said frame; and
- means for receiving and suspending a plurality of existing intra-venous fluid-dispensing bags adjacent to a top portion of said frame;
- wherein said receiving and maintaining means cooperates with said receiving and suspending means so that said frame is balanced at an upright and vertical orientation during transportation between remote locations.

9. The multifunctional medical equipment supporting apparatus of claim 8, wherein said mobile frame comprises:
- a telescopically adjustable shaft including selectively interlocked rectilinear male and female members;
- a concave base member having an annular outer circumference raised above a ground surface, said base member being statically affixed to said female member and spaced from said male member; and
- a plurality of casters pivotally coupled to an underside of said base member and equidistantly juxtaposed along said outer circumference.

10. The multifunctional medical equipment supporting apparatus of claim 9, wherein said receiving and maintaining means comprises:
- a weight member provided with a longitudinal length registered parallel to a longitudinal length of said female member and being spaced therefrom;
- a plurality of rectilinear support arms pivotally coupled directly to said female member, said support arms further being pivotally coupled directly to said weight member; and
- a plurality of anchor brackets pivotally coupled to said supports arms and diametrically offset from said weight member such that said anchor brackets maintain a fixed linear spatial distance from said weight member while traveling along said linear path;
- wherein the existing oxygen tank is removably positioned within said anchor brackets and interfitted therebetween;
- wherein said weight member has a center of mass selectively offset from a center of mass of the existing oxygen tank as the oxygen level is depleted therefrom.

11. The multifunctional medical equipment supporting apparatus of claim 10, wherein each of said support arms has axially opposed first and second ends terminating laterally away from said female member respectively;
- wherein said weight member is pivotally coupled directly to each of said first ends of said support arms such that each of said support arms are synchronously pivoted from a horizontal position to an angularly offset position as said weight member downwardly travels along said linear path, said weight member being vertically oriented and juxtaposed parallel to said female member while said support arms are synchronously pivoted to said angularly offset position.

12. The multifunctional medical equipment supporting apparatus of claim 11, wherein said anchor brackets are pivotally coupled to each of said second ends of said support arms respectively, said anchor brackets being maintained at a horizontal position and further being vertically aligned when said support arms are biased to said angularly offset position and further while said weight member downwardly travels along said linear path.

13. The multifunctional medical equipment supporting apparatus of claim 12, wherein the existing oxygen tank has a center of mass disposed above a center of mass of said weight member after said support arms are pivoted to said angularly offset position.

14. The multifunctional medical equipment supporting apparatus of claim 9, wherein said receiving and suspending means comprises:

a ring and a plurality of coplanar shafts directly coupled thereto, said ring being concentrically attached to said male member, each of said shafts radially extending out from said ring and being equidistantly spaced thereabout, each of said shafts having a curvilinear loop formed at a distal end thereof for receiving one of the plurality of existing intra-venous fluid-dispensing bags respectively.

* * * * *